United States Patent [19]

Kim et al.

[11] Patent Number: 5,273,761
[45] Date of Patent: Dec. 28, 1993

[54] METHOD AND COMPOSITION FOR INSECT CONTROL

[76] Inventors: Yon T. Kim; Jong D. Kim, both of 3113 Nicklas La., #3A, Marina, Calif. 93933

[21] Appl. No.: 831,710
[22] Filed: Feb. 5, 1992

Related U.S. Application Data

[63] Continuation-in-part of Ser. No. 418,579, Oct. 10, 1989, abandoned.

[51] Int. Cl.$^5$ ..................... A61K 33/24; A01N 25/00
[52] U.S. Cl. ....................................... 424/659; 424/84
[58] Field of Search .................................. 424/659, 84

[56] References Cited

FOREIGN PATENT DOCUMENTS 2491296  4/1982  France .
54-017120  2/1979  Japan .

*Primary Examiner*—Frederick E. Waddell
*Assistant Examiner*—T. J. Criares
*Attorney, Agent, or Firm*—Jacques M. Dulin

[57] ABSTRACT

A method of killing roaches and ants by using an insecticidal composition consisting essentially of a mixture of boric acid, sugar, condensed milk, and an aqueous liquefier.

7 Claims, No Drawings

METHOD AND COMPOSITION FOR INSECT CONTROL

CROSS REFERENCE TO RELATED APPLICATION

This is a continuation-in-part of U.S. Ser. No. 07/418,579 filed Oct. 10, 1989, now abandoned.

FIELD

This application relates to an improved method and composition for attracting and killing roaches, ants and flies. More particularly, the invention relates to improved attractant combinations using a toxicant, and attractant, a sweetener, a carrier and a liquefier.

BACKGROUND

Roaches, ants and flies are common pests that have plagued mankind for ages. Extensive efforts have been made to exterminate these difficult and disease-bearing insects.

Boric acid is known as a killing agent in roach and ant-killing compositions. For example, Australian patent 22,579 (Fenwicke, 1935) teaches the use of boric acid as a "germicidal antiseptic" in combination with castor oil and turpentine as "cleaning agents" to be applied to sheep for killing maggots. Japanese patents J5-8052-205 (Nakamoto, 1981), J6-1030-506-A (Wakayama, 1984) and J6-1078-705-A (Amachir, 1984) teach the use of boric acid as the killing agent in various complex compositions for killing roaches (Nakamoto and Amachir) and white ants (Wakayama). All three Japanese patents are dried and used in a pellet, tablet or ball form.

French patent 2,491,296 (Lagache 1982) shows a 50/50 by weight composition of boric acid or one of its salts plus sweetened condensed milk which was placed, without spreading, in a ship's hold to control cockroaches. Japanese document JA-72-23198-R (Sankyo Co. Ltd. 47-23198) shows a toxic roach bait comprising insecticidal compositions, e.g. dieldrin, BHC (Lindane), DDT, Sumithic, and boric acid mixed with more than 4 weight percent glycerol in carriers, such as, cereal, fish meal, rice bran, starch paste, sugar, maltose, fatty acids, faulty acid esters and fatty alcohols. Japanese patent J5-4017-120 (Sakamoto) shows a cockroach bait of 1.5-10 weight percent boric acid, 10-50 weight percent starch and an extract of fish or animal bones prepared by boiling the bones in water for not over 2 hours.

While boric acid has been used previously, the art teaches that it must be kept dry, as wet boric acid will not work; Wellness Letter, University of Calif. at Berkeley, September 1991, page 7. Thus, use of boric acid with aqueous liquefiers, such as water, is not expected to be effective.

The prior art also shows the high degree of specificity of attractants in different insecticide compositions. For example U.S. Pat. No. 4,049,460 (Broadbent, 1977), teaches a composition of brown sugar, a binder material (paraffin or wax), dry dog food, maltose and Dursban (a commercially available insecticide) in pellet form. Roaches are attracted to the dog food, maltose and sugar mixture. The pellets are coated with a paraffin or wax to protect them from disintegrating upon exposure to environmental factors. The Dursban is ingested by the roaches, along with the attractant. Japanese patent J53091-140 (Kao Soap KK) teaches the use of pure concentrated sesame oil, preferably mixed with an extract of cockroaches faeces as an attractant for cockroaches.

U.S. Pat. No. 4,332,792 (Kohn et al., 1982) teaches a process for preparing a pyrolyzate solution of corn syrup and N-methylnicotinic acid for attracting insects, particularly roaches.

U.S. Pat. No. 4,369,176 (Ott, 1983) teaches a sugar, bacteria and carrier material (such as ground corncobs, sawdust or sand) for use as an insect attractant. The sugar is degraded by the bacteria, causing fermentation by-products which are the attractant. The attractant is combined with an insecticide to kill insects. The insects ingest the insecticide along with the composition.

U.S. Pat. No. 4,627,981 (Shimano et al., 1986) discloses the use of various alcohols dissolved in an organic solvent and impregnated on a carrier (such as cardboard or cloth) for use in attracting and killing insects in pellet form.

There is a need in the art for an improved insecticide composition having specific and powerful attractants, having features for direct and easy application, that is not an environmental pollutant or potential carcinogen. Many of the current insecticides are complex organic compounds. Applicants' invention lies in the combination which confers properties of increased efficiency due to direct application of the composition in paste form by squeeze bottle in easily metered amounts to the site of infestation.

THE INVENTION

OBJECTS

It is among the objects of this invention to provide improved compositions for attracting and killing insects, particularly roaches, ants and flies.

It is an other object of the invention to provide improved insecticide compositions employing a toxicant, an optional attractant, a sweetener, a carrier and a liquefier.

Another object of the invention is to provide a safe but effective toxicant that can be used on surfaces such as in kitchens of homes and restaurants.

Another object of the invention is to provide an insecticide composition that can be easily applied directly to areas of infestation and remains active for extended potency.

Still other objects will be evident from the Specification and claims.

SUMMARY

The invention is a composition that exposes insects to a toxicant by means of an attractant, encouraging consumption by means of a sweetener and increased effectiveness by means of an aqueous liquefier that can be reactivated if it dries out.

In the principal embodiment the composition consists of a mixture of boric acid, sugar, condensed milk, and a liquefier selected from water or a bone soup stock, in proportions to form a heavy cream, paste or pellet. Surprisingly, the composition works well even with use of an aqueous liquefier with boric acid. Optionally, an attractant, preferably sesame oil, may be used, but surprisingly, it is effective in very minor volume percentages in the composition. The paste composition is placed in selected locations such that the pests are likely to encounter the substance, but out of the way of normal human traffic.

As a result of experimentation with various different formulations for attracting and killing insects, the present composition was found to exhibit increased power in attracting and killing roaches, ants and flies. In addition, the formulation was found to be resistant to drying out, lasted longer and was easily reactivated.

The composition can be applied to surfaces in kitchens and restaurants. The composition can be applied from a squeeze bottle and easily applied in and around the edges of the area of infestation in easily metered amounts. Barrier lines can be made by squeezing thin ribbons or filaments across insect travel routes, e.g. ant lines. Very importantly it is easy to apply in specified locations as it sticks easily to dry surfaces, including vertical surfaces. Metered amounts in ribbon form can be easily and quickly applied.

The composition once ingested, kills the insects within 3 to 4 days. More importantly, it spoils the eggs carried by the females. Even if the female manages to lay the eggs, they will not hatch. Animals under stress will deliver any eggs they may be carrying. Egg casing is tough and not susceptible to aerosol insecticides. But the if the toxicant is ingested rather than inhaled, the eggs are destroyed even if the female lays them before she dies.

In addition to squeeze bottle application of the cream, the composition can be placed in plastic cups with foil tops, deposited on tape which is stuck to out of the way surfaces, or formed into dry or semi-dry pellets which are placed where needed.

A particularly convenient and preferred means of delivering the composition is to provide it in a plastic squeeze bottle. The composition is made to a creamy paste consistency. It can then be squeezed-out in amounts needed, in droplets or a thin barrier line into corners, around edges, under counter surfaces or placed in any other advantageous location. A most preferred mode of application in the case of ants is to extrude a thin line across an ant pathway so the ants will necessarily come into contact with it, be attracted and eat the composition, ingesting the poisonous boric acid and die.

DETAILED DESCRIPTION OF THE BEST MODE

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

The amounts given in the specific examples are volumetric quantities, and can easily be converted to volume percentages. They can also be then converted to weight percentages by taking into account the specific gravity of the various ingredients. Thus, larger or smaller batches may be prepared.

EXAMPLE 1

A composition in accord with this invention was prepared by mixing (volumetric amounts): 1 teaspoon of sugar, 1 teaspoon of condensed milk (Pet brand), 2 teaspoons of boric acid powder, and 1 teaspoon of water. Note that condensed milk and granular white sugar is used; sweetened condensed milk is not used as it may contain glucose, fructose, corn syrup and other sweeteners in unknown amounts.

The ingredients are thoroughly mixed by hand or mechanically for a few minutes to a creamy consistency and packed in a plastic squeeze bottle with flip-nozzle top. The sugar is first added to and mixed with the condensed milk. After complete dissolution, the boric acid is added and mixed. Finally the water (or soup stock) is added and mixed. Mixing may be accomplished by an eggbeater. The mixing continues until the entire amount of liquefier (water or soup stock) is added, and the resulting composition ranges from a very heavy cream to a paste in consistency. The composition flows easily from the squeeze bottle, but stiffens and "sets" very soon as a paste. It is not a dry hard pellet which can roll away and is impossible to apply to dry vertical surfaces.

Optionally, 1 drop of sesame oil (10 drops=1 teaspoon) may be employed as an attractant, and sufficient food color dye (yellow, blue, red or green) may be included to provide a human recognition "warning" color. Blue is preferred since blue food is unnatural and repugnant to humans. A preservative may also be employed.

As an alternative to water as the liquefier, a bone soup stock may be used. It is made by boiling beef or chicken bones in water to produce a stock rich in calcium and gelatin. This bone soup stock is used in an amount equal to and in place of water, about 1 teaspoon in the formula given above. Meat can be used instead of bones, in which case it should be ground to a creamy consistency.

The composition was delivered by squeezing short ¼"-2" drops and/or ribbons onto surfaces around an area of cockroach, fly and ant infestation, namely below kitchen sinks where they have gone looking for water. A drop is a very short ribbon. The roaches were attracted to or encountered the composition, ate it being stimulated by the sweeteners, and died in three to four days. In addition, it was observed that the roach egg cases did not hatch, being spoiled.

Examination of the creamy ribbons showed eaten areas. The insect kill was extensive; carcasses of roaches, ants and flies were observed within 3 to 4 days and removed. After a second application one week later, reported roach sightings and evidence (egg cases, nibbled food and excrement pellets) were negligible. Thus the treatment with the composition of the invention was successful after commercial insecticide sprays proved too hazardous and essentially ineffective.

EXAMPLE 2

The composition of Example 1 was extruded into individual droplets and short strips (¼-½" in length), then let dry to form pellets. The pellets were placed into an area of roach infestation. Extensive roach kill was observed within a few days, similar to Example 1. Several of the remaining pellets were collected, moistened with hot water and worked with a spoon or spatula into a creamy paste of desired consistency. This paste was re-extruded, and continued to be effective as evidenced by being eaten by roaches followed by kill as seen from carcasses.

It should be understood that various modifications within the scope of this invention can be made by one of ordinary skill in the art without departing from the spirit thereof. We therefore wish our invention to be defined by the scope of the appended claims as broadly as the prior art will permit, and in view of the specification if need be.

We claim:

1. A method of killing roaches and ants comprising the steps of:
   a) providing an insecticidal composition consisting essentially of an intimate admixture of:
      i) 2 parts by volume boric acid;
      ii) 1 part by volume sugar;
      iii) 1 part by volume condensed milk; and
      iv) 1 part by volume of an aqueous liquefier selected from water, a bone or meat soup stock, and mixtures thereof; said mixture having a consistency ranging from a heavy cream to a paste;
   b) applying said insecticidal mixture composition paste onto dry surfaces where said roaches or ants will come into contact therewith; and
   c) said application step comprising extrusion of ribbons or droplets onto said surfaces.

2. A method as in claim 1 wherein:
   a) said composition is packed in a squeeze bottle, and said application includes squeezing amounts of said composition onto said surface.

3. A method as in claim 2 wherein:
   a) said composition additionally includes 0.1 part by volume sesame oil as an attractant.

4. A method as in claim 2 wherein:
   a) said composition includes up to one part by volume bone or meat soup stock in place of an equal amount of said water.

5. A method as in claim 2 wherein:
   a) said extrusion comprises extruding a plurality of ribbons of length of from about ¼" to 2" in length spaced about an area frequented by roaches.

6. A method as in claim 2 wherein:
   a) said composition additionally includes a preservative.

7. A method as in claim 6 wherein:
   a) said composition includes a dye.

* * * * *